(12) United States Patent
Park et al.

(10) Patent No.: US 9,469,663 B2
(45) Date of Patent: Oct. 18, 2016

(54) OPTICALLY COMPENSATED ACRYLIC PRESSURE-SENSITIVE ADHESIVE COMPOSITION, POLARIZING PLATE AND LIQUID CRYSTAL DISPLAY DEVICE CONTAINING THE SAME

(75) Inventors: Seung Joon Park, Daejeon (KR); No Ma Kim, Daejeon (KR); In Cheon Han, Seoul (KR); Kee Young Kim, Seoul (KR); Jeong Min Ha, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1357 days.

(21) Appl. No.: 12/449,066

(22) PCT Filed: Oct. 22, 2007

(86) PCT No.: PCT/KR2007/005166
§ 371 (c)(1),
(2), (4) Date: Jul. 19, 2010

(87) PCT Pub. No.: WO2008/091050
PCT Pub. Date: Jul. 31, 2008

(65) Prior Publication Data
US 2010/0297368 A1 Nov. 25, 2010

(30) Foreign Application Priority Data

Dec. 20, 2006 (KR) ........................ 10-2006-0130718

(51) Int. Cl.
*C09K 19/00* (2006.01)
*C07F 9/58* (2006.01)
*G02F 1/1335* (2006.01)

(52) U.S. Cl.
CPC .......... *C07F 9/582* (2013.01); *G02F 1/133528* (2013.01); *G02F 2202/28* (2013.01); *Y10T 428/1036* (2015.01); *Y10T 428/1059* (2015.01); *Y10T 428/1082* (2015.01)

(58) Field of Classification Search
CPC .................. Y10T 428/1082; Y10T 428/1059; Y10T 428/1036; Y10T 428/105; Y10T 428/10; Y10T 428/2852; Y10T 428/2891; C08F 220/18; C09J 133/04; C09J 133/066; C09J 133/064; C09J 133/08; C09J 133/10; C09J 133/02; C09J 135/06; G02B 5/3033; G02F 2202/28; G02F 1/133528
USPC ........ 428/1.31, 1.5, 1.55; 524/558; 525/210, 525/218, 221, 222, 223
See application file for complete search history.

(56) References Cited

U.S. PATENT DOCUMENTS

| | | | |
|---|---|---|---|
| 5,310,835 A | 5/1994 | Skoultchi et al. | |
| 5,852,119 A * | 12/1998 | Kojima et al. | 525/123 |
| 6,602,944 B2 | 8/2003 | Vaidya | |
| 2003/0032715 A1* | 2/2003 | Sakaitani et al. | 524/558 |
| 2005/0117217 A1 | 6/2005 | Yamaoka et al. | |
| 2005/0181148 A1* | 8/2005 | Kim et al. | 428/1.55 |
| 2008/0033109 A1* | 2/2008 | Tomita et al. | 525/100 |

FOREIGN PATENT DOCUMENTS

| | | |
|---|---|---|
| CA | 2386847 A1 * | 5/2001 |
| JP | 10-279907 A | 10/1998 |
| KR | 10-2000-0067624 | 11/2000 |
| KR | 10-2005-0102997 | 10/2005 |
| KR | 10-2006-0108515 | 10/2006 |
| WO | WO 2006-009250 | 1/2006 |
| WO | WO 2006/009250 A1 | 1/2006 |

* cited by examiner

*Primary Examiner* — Ruiyun Zhang
(74) *Attorney, Agent, or Firm* — Dentons US LLP

(57) ABSTRACT

The present invention relates to an acrylic pressure-sensitive adhesive composition, a polarizing plate and a liquid crystal display device, using the same. More specifically, the present invention relates to an acrylic pressure-sensitive adhesive composition having optimal stress releasing property which comprises an optically compensated acrylic copolymer (A) containing a cross-linkable functional group, an optically compensated acrylic copolymer (B) containing no cross-linkable functional group, and a multi-functional cross-linking agent (C). A polarizing plate and a liquid crystal display device comprising the pressure-sensitive adhesive composition meets with major properties such as adhesion endurance reliability, with effectively providing optical compensation effect and stress release effect, and has an effect of improving a light leakage phenomenon.

17 Claims, No Drawings

OPTICALLY COMPENSATED ACRYLIC PRESSURE-SENSITIVE ADHESIVE COMPOSITION, POLARIZING PLATE AND LIQUID CRYSTAL DISPLAY DEVICE CONTAINING THE SAME

This application claims the benefit of Korean Patent Application No. 10-2007-0006966 filed on Jan. 23, 2007 and PCT Application No. PCT/KR2007/005166, filed on Oct. 22, 2007, which is hereby incorporated by reference for all purposes as if fully set forth herein.

TECHNICAL FIELD

The present invention relates to an acrylic pressure-sensitive adhesive composition for a polarizing plate. More specifically, the present invention relates to a pressure-sensitive adhesive composition for a polarizing plate having an excellent low light leakage property, without changing major properties under high temperature, or high temperature and humidity conditions such as endurance reliability and workability, and a polarizing plate and a liquid crystal display device, containing the same.

BACKGROUND ART

Generally, in preparing liquid crystal display devices, liquid crystal cells comprising liquid crystals and polarizing plates are basically required and suitable adhesive layers or pressure-sensitive adhesive layers have to be used for binding them. In addition, for improving functions of liquid crystal display devices, a phase retardation plate, a compensation plate for wide view angle, a brightness enhancement film, and the like may be used, with additionally adhered to the polarizing plate.

Major structure forming a liquid crystal display device comprises, generally, a uniformly aligned liquid crystal layer, a polarizing plate with a multi-layer structure, incorporated into a pressure-sensitive adhesive layer or an adhesive layer, based on a liquid crystal cell consisted of a transparent glass plate or plastic sheet material containing a transparent electrode layer; a phase retardation plate; and an additional functional film layer and the like.

The structure of polarizing plate is one comprising an iodine compound or a dichroic polarizing material aligned in a certain direction. To protect these polarizing elements, multi-layers are formed on both sides using a protective film such as triacetyl cellulose (TAC). In addition, the polarizing plate may additionally comprise a phase retardation film, or a compensation film for wide view angle such as a liquid crystal type film, in a shape having a unidirectional molecular alignment.

The aforementioned films are made of materials having different molecular structures and compositions, and so have different physical properties. Especially, under high temperature, or high temperature and humidity conditions, the dimensional stability according to shrinkage or expansion of materials having a unidirectional molecular alignment is insufficient. As a result, if the polarizing plate is fixed by a pressure-sensitive adhesive, then stress is concentrated on the TAC layer by shrinkage or expansion under high temperature, or high temperature and humidity conditions, thereby birefringence is developed and light leakage occurs. In this case, a negative birefringence is usually caused over the layer by the shrunk TAC.

Meanwhile, the pressure-sensitive adhesive layer needs high cohesion strength at high temperature to maintain the endurance reliability, for which partially cross-linked visco-elastic materials are used. When the partially cross-linked structure is introduced into the pressure-sensitive layer, the pressure-sensitive layer has the residual stress under the given stress and the polymer in the cross-linked structure is aligned in the specific direction to develop birefringence. Under such alignment, general alkyl acrylic pressure-sensitive adhesives develop birefringence of negative values as in TAC.

Meanwhile, monitor size of computers, and the like, becomes larger, and the demand is recently rapidly increased for LCD TVs using polarizing plates. As such panels become larger, polarizing plates also become larger, and thereby the residual stresses of the layers of TAC and the pressure-sensitive adhesive becomes higher and thereby the negative birefringence is increased and thus light leakage is extremely increased.

Among methods of minimizing light leakage under sixth residual stresses, a method may be considered, such as a method that an overall birefringence, including a TAC layer and pressure-sensitive adhesive, under the residual stress is minimized by adding (blending) materials representing birefringence of positive values to the final pressure-sensitive adhesive layer or copolymerizing acrylic monomers having a positive birefringence.

KR laid-open patent publication No. 2003-0069461 discloses a pressure-sensitive adhesive correcting birefringence of negative values that the acrylic pressure-sensitive adhesive layer represents under the residual stress by incorporating 0.01 to 40 parts by weight of a low molecular weight material representing birefringence of positive values under the residual stress into the acrylic pressure-sensitive adhesive layer. However, in said pressure-sensitive adhesive, the modulus of pressure-sensitive adhesive is lowered, due to the incorporated low molecular weight material therein. Therefore, there is a problem in tailoring property on processing the polarizing plate. In addition, there are a problem of moving the low molecular weight material into the interface for long-term storage and the possibility of phase separation with the acrylic pressure-sensitive adhesive.

A method of minimizing birefringence by copolymerizing a monomer representing negative birefringence and a monomer representing positive birefringence under the residual stress is also known (refer to Applied Optics (1997)). In a specific example, the degree of birefringence may be regulated under the given stress by copolymerizing an acrylic monomer (negative birefringence) having a side chain of an alkyl group and an acrylic monomer (positive birefringence) having a side chain of an aromatic group.

JP Unexamined Patent Publication No. 2002-332468 describes a method of improving plastic resistance of the pressure-sensitive adhesive layer by introducing an acrylic monomer containing an aromatic group in a side chain. In addition, U.S. Pat. No. 6,663,978, and JP Unexamined Patent Publication Nos. 2002-173656 and 2003-013029 describe a method of regulating a refractive index of a pressure-sensitive adhesive layer by introducing an acrylic monomer containing an aromatic group in a side chain. Further, JP Unexamined Patent Publication No. 2005-053976 describes a method of improving adhesion performance in even low polar films by introducing an acrylic monomer containing an aromatic group in a side chain.

DISCLOSURE OF INVENTION

Technical Problem

However, in the prior disclosures above, there are not notified technical ideas of attempting optical compensation which regulates birefringence under the residual stress to improve the light leakage phenomenon, when acrylic pressure-sensitive adhesives for polarizing plates are prepared by introducing an acrylic monomer containing an aromatic group in a side chain.

Technical Solution

The present invention is intended to solve the above conventional problems, and one object of the present invention is to provide a pressure-sensitive adhesive composition for a polarizing plate having an excellent low light leakage property by regulating birefringence such that it has positive values under the residual stress, without changing major properties under high temperature, or high temperature and humidity conditions such as endurance reliability and workability, using a (meth)acrylic copolymer having optimal stress releasing property which comprises an optically compensated acrylic copolymer (A) containing a cross-linkable functional group, an optically compensated acrylic copolymer (B) not containing cross-linkable functional group, and a multi-functional cross-linking agent (C), as a pressure-sensitive adhesive layer.

Another object of the present invention is to provide a polarizing plate using the acrylic pressure-sensitive adhesive composition with said characteristics.

The other object of the present invention is to provide a liquid crystal display device comprising a polarizing plate prepared by the acrylic pressure-sensitive adhesive composition with said characteristics.

BEST MODE FOR CARRYING OUT THE INVENTION

The present invention relates to an acrylic pressure-sensitive adhesive composition which comprises an acrylic copolymer (A) containing i) 50 to 75 parts by weight of an alkyl(meth) acrylic acid ester monomer having alkyl of 2 to 14 carbon atoms, 25 to 50 parts by weight of an acrylic ester monomer including an aromatic group copolymerizable with said acrylic monomer, and 0.1 to 10 parts by weight of a vinyl or acrylic ester monomer including a cross-linkable functional group;

an acrylic copolymer (B) containing i) 50 to 75 parts by weight of an alkyl(meth)acrylic acid ester monomer having alkyl of 2 to 14 carbon atoms, and 25 to 50 parts by weight of an acrylic ester monomer including an aromatic group copolymerizable with said acrylic monomer; and a multi-functional cross-linking agent (C) cross-linkable with an acrylic ester monomer including a cross-linkable functional group of above.

To improve the light leakage phenomenon, a method of contributing a stress releasing function to the pressure-sensitive adhesive via adding a plasticizer or a low molecular weight material to a high molecular weight copolymer, or regulating a cross-linking structure has generally been used. However, it is difficult to completely inhibit the light leakage phenomenon of polarizing plate via only stress release. This is because the residual stress in the pressure-sensitive adhesive layer represented by such cross-linked structure cannot be completely removed, although partially cross-linked structure should be introduced into the adhesive to maintain the endurance reliability of the pressure-sensitive adhesive for polarizing plates. Therefore, a negative birefringence is present in the alkyl acrylate pressure-sensitive adhesive layer generally used under such residual stress, which is a major cause that cannot improve the light leakage any longer, together with a negative birefringence present in the contracted TAC layer. To offset such negative birefringence occurred in such pressure-sensitive adhesive layer, it may be allowed to introduce (optically compensate) a pressures-sensitive adhesive layer copolymerizing acrylic monomer (acrylic monomer containing an aromatic group) representing a positive birefringence into the pressure-sensitive adhesive layer. However, when the light leakage is improved by simply using such optical compensation, a large quantity of aromatic-containing acrylic monomer is required, and thereby there is a side effect that adhesion strength of a pressure-sensitive adhesive is greatly increased. This adversely affects re-releasability as a major function of the pressure-sensitive adhesive for polarizing plates. Therefore, to inhibit the light leakage of polarizing plates as much as possible, with maintaining the endurance reliability and the re-releasability as a major function of the adhesives for polarizing plates, it is necessary to simultaneously render a suitable level of optical compensation, with maximizing the stress release function of the pressure-sensitive adhesive through introducing the optimal cross-linked stricture.

Thus, the present invention is characterized by having the optimal cross-linking structure which can minimize the light leakage phenomenon, with maintaining major functions of the pressure-sensitive adhesive, using a mixture of an optically compensated acrylic copolymer (A) containing a cross-linkable functional group and an optically compensated acrylic copolymer (B) containing no cross-linkable functional group.

In order for the acrylic pressure-sensitive adhesive composition according to the present invention to have such optimal cross-linking stricture, a weight ratio of an acrylic copolymer (A) and an acrylic copolymer (B) is preferably 1:9 to 4:1.

When the ratio of acrylic copolymer (A) is less than that of acrylic copolymer (B), it is hard to obtain sufficient cohesion strength. Therefore, said ratio is suitably more than 1:9, and more preferably more than 1:4. In addition, when the ratio of acrylic copolymer (A) to acrylic copolymer (B) is more than 4:1, the ratio of cross-linkable copolymer is increased. As a result, it is difficult to control the degree of cross-linking and improve the light leakage through the stress release of the pressure-sensitive adhesive in combination with the effect of optical compensation.

In addition, it is preferred in the acrylic pressure-sensitive adhesive composition according to the present invention that weight average molecular weights of acrylic copolymer (A) and acrylic copolymer (B) are each independently 800,000 to 2,000,000.

If said weight average molecular weight is less than 800,000, cohesion strength is so impaired that endurance reliability is poor. If said weight average molecular weight is more than 2,000,000, the effect of stress release is so impaired that the effect of light leakage is slight.

Each component in the present composition is specifically explained below.

Acrylic Copolymers (A) and (B)

i) Alkyl(Meth)Acrylic Add Ester Monomer

The acrylic copolymer (A) and the acrylic copolymer (B), according to the present invention, as major resins include i) 50 to 75 parts by weight of alkyl(meth)acrylic acid ester monomer in which alkyl has 2 to 14 carbon atoms. i) Alkyl(meth) acrylic acid ester monomer included in said acrylic copolymer (A) and acrylic copolymer (B) may be the same or different.

If the amount of said i) alkyl(meth)acrylic acid ester monomer is in excess of 75 parts by weight, the final pressure-sensitive adhesive represents high negative birefringence under the residual stress and thus the effect of improving optical light leakage may be slight. In addition, if the amount of said i) alkyl(meth)acrylic acid ester monomer is less than 50 parts by weight, the adhesion property balance of final pressure-sensitive adhesive is deteriorated, the adhesive represents high positive birefringence under the residual stress and thus the effect of improving optical light leakage is deteriorated.

The i) alkyl(meth)acrylic acid ester monomer in which alkyl has 2 to 14 carbon atoms preferably uses one or more selected from the group consisting of ethyl (meth)acrylate, n-propyl(meth)acrylate, isopropyl(meth)acrylate, n-butyl (meth)acrylate, t-butyl(meth)acrylate, sec-butyl(meth)acrylate, pentyl(meth)acrylate, 2-ethylhexyl(meth)acrylate, n-octyl(meth)acrylate, isooctyl(meth)acrylate, isononyl (meth)acrylate, lauryl(meth)acrylate, and tetradecyl(meth) acrylate. If the carbon number of alkyl is departed from the above range, the glass transition temperature (Tg) of the pressure-sensitive adhesive is increased, or regulation of the adhesive property is difficult. Therefore, the carbon number is limited within a range of 2-14.

ii) Aromatic-Containing (Meth)Acrylic Monomer

The acrylic copolymer (A) and the acrylic copolymer (B), according to the present invention are monomers representing birefringence of positive values under stress, for compensating birefringence of negative values in acrylic copolymer comprising alkyl(meth)acrylic acid ester monomer in which alkyl has 2 to 14 carbon atoms as a principal component, and include ii) 25 to 50 parts by weight of acrylic ester monomer containing an aromatic group copolymerizable with said acrylic monomer alkyl(meth)acrylic acid ester monomer. ii) Acrylic ester monomer containing an aromatic group included in said acrylic copolymer (A) and acrylic copolymer (B) may be the same or different.

The amount of said (meth)acrylic ester monomer containing aromatic group is suitably 25 to 50 parts by weight in all monomers. If the amount of (meth)acrylic ester monomer containing aromatic group is less than 25 parts by weight in all monomers, the final pressure-sensitive adhesive represents large negative birefringence under the residual stress and thus the effect of improving optical light leakage is slight. If the amount is in excess of 50 parts by weight, the adhesion property balance of final pressure-sensitive adhesive is deteriorated. Especially, the adhesion strength is greatly raised, so that the re-releasability of polarizing plates is mach deteriorated.

The (meth)acrylic acid ester monomer containing a copolymerizable aromatic group according to the present invention uses, preferably, a compound of Formula 1:

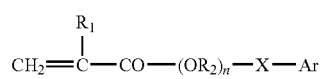

wherein,
$R_1$ represents hydrogen or a methyl group,
$R_2$ represents an alkylene group having 1 to 12 carbon atoms,
n represents an integer of 0 to 3, preferably, 0 or 1,
X represents an oxygen atom, a sulfur atom or an alkylene group having 1 to 4 carbon atoms and
Ar represents an aromatic group unsubstituted or substituted with halogen, particularly bromo or chloro, or alkyl of 1 to 12 carbon atoms.

Preferred examples of said compound of Formula 1 include, but not limited to, phenoxy ethyl(meth)acrylate, benzyl(meth)acrylate, 2-phenylthio-1-ethyl (meth)acrylate, 6-(4,6-dibromo-2-isopropylphenoxy)-1-hexyl(meth)acrylate, 6-(4,6-dibromo-2-sec-butylphenoxy)-1-hexyl(meth) acrylate, 2,6-dibromo-4-nonylphenyl(meth)acrylate, 2,6-dibromo-4-dodecyl phenyl (meth)acrylate, 2-(1-naphtyloxy)-1-ethyl(meth)acrylate, 2-(2-naphtyloxy)-1-ethyl (meth) acrylate, 6-(1-naphtyloxy)-1-hexyl(meth)acrylate, 6-(2-naphtyloxy)-1-hexyl (meth)acrylate, 8-(1-naphtyloxy)-1-octyl(meth)acrylate, and 8-(2-naphtyloxy)-1-octyl (meth) acrylate. Said compound of Formula 1 may be used alone or in a form of a mixture thereof.

More preferably, said compound of Formula 1 is phenoxy ethyl(meth)acrylate, benzyl(meth)acrylate, 2-phenylthio-1-ethyl acrylate, 8-(2-naphtyloxy)-1-octyl acrylate, 2-(1-naphtyloxy)-1-ethyl acrylate and a mixture thereof; and most preferably, phenoxy ethyl(meth)acrylate, benzyl(meth)acrylate or a mixture thereof.

iii) Cross-Linkable Monomer

In the acrylic copolymer (A) according to the present invention, iii) a vinyl or acrylic ester monomer containing a cross-linkable functional group is for regulating adhesion strength and cohesion strength of the acrylic copolymer, and preferably includes an acid group or a hydroxyl group within its stricture.

The vinyl monomer containing an acid group used herein is a component for reacting with a cross-linking agent and giving the pressure-sensitive adhesive cohesion strength by chemical bonds such that cohesion failure of the adhesive is not occurred on raising temperature.

Said copolymerizable monomer containing an acid group may include one or more selected from the group consisting of a copolymerizable monomer containing a carboxyl group or anhydride thereof, a copolymerizable monomer containing a sulfonic acid group, and a copolymerizable monomer containing a phosphoric acid group.

The copolymerizable monomer containing a carboxyl group above is (meth)acrylic acid, carboxyethyl acrylate, carboxypentyl acrylate, itaconic acid, maleic acid, fumaric acid, or crotonic acid;

the anhydride of copolymerizable monomer containing a carboxyl group is maleic anhydride or itaconic anhydride;

the copolymerizable monomer containing a sulfonic acid group is styrene sulfonic acid, allyl sulfonic acid, 2-(meth) acrylamide-2-methyl propane sulfuric acid, (meth)acrylamide propane sulfuric acid, sulfopropyl(meth)acrylate, (meth) acryloyloxy naphthale sulfuric acid; and the copolymerizable monomer containing a phosphoric acid group may be selected from 2-hydroxyethyl acryloyl phosphate, and the like, without limitation.

In addition, the vinyl or acrylic monomer containing a hydroxyl group is preferably one or more selected from the group consisting of 2-hydroxyethyl(meth)acrylate, 2-hydroxypropyl(meth)acrylate, 4-hydroxybutyl(meth)acrylate, 2-hydroxyethyleneglycol (meth)acrylate, and 2-hydroxypropyleneglycol (meth)acrylate.

If the amount of said vinyl or acrylic monomers containing an acid group or a hydroxyl group in the acrylic copolymer (A) is too much, adhesion is lowered, and release strength is lowered. Therefore, its amount in all monomers is preferably used in a range of 0.01 to 10 parts by weight.

iv) Functional Monomer

To regulate the glass transition temperature of the pressure-sensitive adhesive or provide other functionalities, it is preferred that the (meth)acrylic copolymers (A) and (B) according to the present invention, each independently, further comprises 0-20 parts by weight of functional monomer iv) of Formula 2 based on weight of total monomers as an optional component.

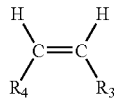

wherein, $R_4$ represents hydrogen or alkyl, $R_3$ represents cyano, phenyl unsubstituted or substituted with alkyl, acetyloxy, or $COR_5$, where $R_5$ represents amino or glycidyloxy unsubstituted or substituted with alkyl.

In the formula above, the alkyl of $R_3$ to $R_5$ preferably, represents lower alkyl of 1 to 6 carbon atoms, and more preferably, methyl or ethyl.

Examples of said compound of Formula 2 may include, but not limited to, styrene monomers such as styrene or alpha methyl styrene; carboxylic acid vinyl esters such as vinyl acetate; or vinyl monomers containing nitrogen such as acrylonitrile, (meth)acryl amide, N-methyl(meth)acryl amide, N-butoxy methyl(meth)acryl amide, or glycidyl (meth)acrylate. Said monomers may be used alone or by mixing two or more thereof.

If the amount of said functional monomer iv) of Formula 2 is too high, the flexibility and the peel strength of pressure-sensitive adhesive are lowered. Therefore, it is preferred to use less than 20 parts by weight of total monomer components.

v) Polymerization Method

The method for preparing the acrylic copolymers (A) and (B) according to the present invention is not specifically limited, and the (meth)acrylic copolymer can be prepared by solution polymerization, photo-polymerization, bulk polymerization, suspension polymerization, or emulsion polymerization. Preferably, it is prepared by using solution polymerization. The polymerization temperature is preferably 50 to 140?, and the initiator is preferably added in a state that monomers are evenly mixed.

Such polymerization initiator may use an azo-based polymerization initiator such as azo-bisisobutyronitrile and azobiscyclohexanecarbonitrile, or peroxide such as benzoyl peroxide and acetyl peroxide alone or in a mixture thereof.

Multi-Functional Cross-Linking Agent (C)

To cross-link the acrylic copolymer (A), the acrylic pressure-sensitive adhesive composition of the present invention may comprises 0.01 to 10 parts by weight of multi-functional cross-linking agent (C) based on 100 parts by weight of the (meth) acrylic copolymer. The preferred physical properties may be provided within the above ranges.

Said multi-functional cross-linking agent (C) is reacted with a carboxylic group and a hydroxyl group, and the like, to serve to increase the cohesion strength of pressure-sensitive adhesive.

Preferably, said multi-functional cross-linking agent is one or more selected from the group consisting of isocyanate compounds, epoxy compounds, aziridine compounds, and metal chelate compounds. Among these, isocyanate compounds is easy to be used for use propose.

Said isocyanate compounds may be one or more selected from the group consisting of tolylene diisocyanate, xylene diisocyanate, diphenylmethane diisocyanate, hexamethylene diisocyanate, isoform diisocyanate, tetramethylxylene diisocyanate, naphthalene diisocyanate, and their reactants with polyol (trimethylolpropane, etc.), said epoxy compounds may be one or more selected from the group consisting of ethyleneglycol diglycidylether, triglycidylether, trimethylolpropane triglycidylether, N,N,N',N'-tetraglycidylethylenediamine, and glycerine diglycidylether, said aziridine compounds may be one or more selected from the group consisting of N,N'-toluene-2,4-bis(1-aziridinecarboxide), N,N'-diphenylmethane-4,4'-bis(1-aziridinecarboxide), triethylenemelamine, bisiso-prothaloyl-1-(2-methylaziridine), and tri-1-aziridinylphosphineoxide, said metal chelate compounds may use, but not limited to, one or more selected from compounds that a multivalent metal such as aluminum, iron, zinc, tin, antimony, magnesium and vanadium is coordinated with acethylacetone or ethyl acetoacetate.

The multi-functional cross-linking agent may be evenly coated when the functional cross-linking reaction of the cross-linking agent is hardly warred in the combining process performed for forming the pressure-sensitive adhesive layer. If the coating process is completed followed by drying and aging, the cross-linked structure may be formed to obtain the pressure-sensitive adhesive layer having elasticity and strong cohesion strength.

Additives

In addition, if the present composition is adhered to a glass substrate, it may further comprises a silane coupling agent for improving adhesion stability and thus more improving heat resistance/moisture resistance. When the glass substrate is left for a long time under a high temperature and humidity, such silane coupling agent serves to be of help to improve adhesion reliability, which may be used in an amount of 0.005 to 5 parts by weight based on 100 parts by weight of all the acrylic copolymers. If the amount is less than 0.005 parts by weight, the adhesion reliability is not improved. If the amount is in excess of 5 parts by weight, the endurance reliability is lowered.

The silane coupling compound is g-glycydoxypropyl trimethoxysilane, g-glycydoxypropyl methyldiethoxysilane, g-glycydoxypropyl triethoxysilane, 3-mercaptopropyl trimethoxysilane, vinyl trimethoxysilane, vinyl triethoxysilane, g-methacryloxypropyl trimethoxysilane, g-methacryloxypropyl triethoxysilane, g-aminopropyl triethoxysilane, 3-isocyanatepropyl triethoxysilane, or g-acetoacetatepropyl trimethoxysilane and the like. These may be used alone or in a mixture thereof.

The present invention may further comprise a tackifier resin, which may be used in an amount of 1 to 100 parts by weight based on 100 parts by weight of the acrylic copolymer (A). If the amount is less than 1 part by weight, the tackifying function is poor. If the amount is in excess of 100 parts by weight, the compatibility or the cohesion strength of pressure-sensitive adhesive is often reduced.

The tackifier resin may use a (hydrogenated) hydrocarbon resin, a (hydrogenated) rosin resin, a (hydrogenated) rosin ester resin, a (hydrogenated) terpene resin, a (hydrogenated) terpene phenol resin, a polymerized rosin resin, or a polymerized rosin ester resin, and the like. These may be used alone or by mixing two or more of the above resins.

In addition, for special purposes, acrylic low molecular weight polymers, an epoxy resin, a hardener, etc. may be additionally mixed and used, and for general purposes, a UV stabilizer, an antioxidant, a colorant, a reinforcing agent, a filler, a defoaming agent, a surfactant, a plasticizer, etc. may be properly added and used.

In addition, the present invention relates to a polarizing plate characterized by comprising
a polarizing film; and
a pressure-sensitive adhesive layer containing said acrylic pressure-sensitive adhesive composition according to the present invention.

The present polarizing plate comprises a pressure-sensitive adhesive layer formed from the above pressure-sensitive adhesive composition on one side or both sides of the polarizing film. Polarizing films or polarizing devices composing the polarizing plate are not specifically limited.

For example, said polarizing film is a film that a polarizing component such as iodine or dichroic dye is contained in polyvinyl alcohol resin film to elongate the resulting product. The thickness of these polarizing films is also not specifically limited, and may form usual thickness. Said polyvinyl alcohol resin may use polyvinyl alcohol, polyvinyl formal, polyvinyl acetal and saponified ethylene vinyl acetate copolymer, and the like.

On both sides of the polarizing film, multilayer films may be formed, on which a protective film is laminated, such as a cellulose film, for example, triacetyl cellulose, etc.; a polyester film, for example, polycarbonate, or polyethylene terephthalate, etc.; a polyether film, for example, polyether sulfone; a polyolefin film, for example, polyethylene, polypropylene, polyolefin having cyclo or norbornene structure, or ethylene propylene copolymer. The thickness of these protective films is not specifically limited, and may form usual thickness.

The method of forming the pressure-sensitive adhesive layer on a polarizing film is not specifically limited in the present invention, which may be applied by a method of coating the pressure-sensitive adhesive directly on the surface of a polarizing film, using a bar water and the like, and drying the adhesive, or a method of coating the pressure-sensitive adhesive on a surface of releasable substrate, drying the adhesive, transferring the pressure-sensitive adhesive layer formed on the surface of said releasable substrate to the surface of polarizing film, and aging the layer.

In addition, on the polarizing plate of the present invention may be laminated one or more layers providing additional functions, such as protective layer, reflecting layer, anti-glare layer, phase retardation plate, compensation film for wide view angle, and brightness enhancing film. Said pressure-sensitive adhesive layer according to the present invention may also be attached to said functional layers.

The polarizing plate applied by the pressure-sensitive adhesive of the present invention can be applied to all usual liquid crystal display devices, the kind of which liquid crystal panel is not specifically limited. Preferably, the present invention may construct liquid crystal display devices comprising a liquid crystal panel binding the pressure-sensitive adhesive polarizing plate to one side or both sides of a liquid crystal cell.

The present invention is explained in more detail through examples and comparative examples below. The examples are provided to help the specific understanding of the present invention, but the scope of the present invention is not restricted to these examples.

Preparation Example 1

To 1 L reactor equipped with a cooling system for reflux of nitrogen gas and easy regulation of temperature a mixture of monomers consisting of 68 parts by weight of n-butylacrylate (BA), 2.0 parts by weight of hydroxymethacrylate, and 33 parts by weight of benzyl acrylate, as the composition represented in Table 1 below, was added. Then, 150 parts by weight of ethyl acetate (EAc) was added thereto as a solvent. To remove oxygen, nitrogen gas was purged for 60 minutes, and the temperature was kept at 60° C. 0.03 Parts by weight of azobisisobutyronitrile (AIBN), a reaction initiator, was added thereto and reacted for 8 hours. After the reaction, the resulting product was diluted with ethyl acetate (EAc) to prepare an acrylic copolymer (A-1) having a solid content of 20% by weight, a weight average molecular weight of 1,200,000.

Preparation Example 2-8

High molecular weight acrylic copolymers were prepared without adding some of each component or with partially adding them in Preparation Example 1, as shown in Table 1 below. Their results were represented in Table 1.

TABLE 1

|  |  |  | Preparation Example | | | | | | | |
|---|---|---|---|---|---|---|---|---|---|---|
|  | Symbol | Component | 1 | 2 | 3 | 4 | 5 | 6 | 7 | 8 |
| Copolymer Composition (part by weight) | i) | n-BA | 68 | 63 | 43 | 88 | 70 | 65 | 45 | 90 |
|  | ii) | BzA | 30 |  | 55 | 10 | 30 |  | 55 | 10 |
|  |  | PHEA |  | 35 |  |  |  | 35 |  |  |
|  | iii) | 2-HEMA | 2 |  |  | 2 | 2 |  |  |  |
|  |  | AA |  | 2 |  |  |  |  |  |  |
|  | (C) | AIBN | 0.03 | 0.03 | 0.03 | 0.03 | 0.03 | 0.03 | 0.03 | 0.03 |
|  | Solvent | EAc | 120 | 120 | 150 | 150 | 120 | 150 | 150 | 120 |
| Mw (10,000) |  |  | 150 | 150 | 120 | 160 | 160 | 155 | 125 | 160 | n-BA: n-butylacrylate, BzA: benzyl acrylate, PHEA: phenoxy ethyl acrylate, 2-HEMA: 2-hydroxyethylmethacrylate, AA: acrylic acid, AIBN: azobisisobutyronitrile, EAc: ethylacetate Example 1

Combination

20 Parts by weight of the obtained high molecular weight acrylic copolymer in Preparation Example 1 and 80 parts by weight of the obtained high molecular weight acrylic copolymer in Preparation Example 5 were homogenously mixed and 0.1 parts by weight of tolylene diisocyanate addict of trimethylolpropane (TDI-1) and 0.1 parts by weight of -glycidoxypropyltrimethoxysilane as a multi-functional cross-linking agent were added. The mixture was diluted in a suitable concentration and homo-geneously mixed, considering the coating property. The resulting product was coated on a releasing sheet and dried to obtain a 30 microns homogenous pressure-sensitive adhesive layer.
<Laminating Procedure>

The prepared pressure-sensitive adhesive layer above was subjected to adhesion to a iodine polarizing plate with a thickness of 185 microns. The resulting polarizing plate was cut into proper sizes and evaluated. The results evaluated for the polarizing plate on which the pressure-sensitive adhesive was applied were represented in Table 2 below.

Examples 2-3

Acrylic copolymers were subjected to combination and laminating procedure by the same method as Example 1, wherein some were not combined or partially combined, based on combinations in Example 1, as combination ratios in Table 2 below. Then, endurance reliability and uniformity of light transmission were evaluated by the same method as Example 1 and the results were represented in Table 2 below.

Comparative Examples 1-4

Acrylic copolymers were subjected to combination and laminating procedure by the same method as Example 1, wherein some were not combined or partially combined, based on combinations in Example 1, as combination ratios in Table 2 below. Then, endurance reliability and uniformity of light transmission were evaluated by the same method as Example 1 and the results were represented in Table 2 below.

Experimental Example

1. Re-Releasability

The polarizing plate coated with the pressure-sensitive adhesive was cut into 90 mm wide and 170 mm long, and then adhered to an alkali-free plate glass by Corning, Inc. using a laminator. Then, the plate glass was left in the Temperature and Humidity Room Chamber for 1 hour, heated at 50° C. for 4 hours and left at room temperature for 1 hour, followed by releasing the polarizing plate from the glass. The re-releasability was evaluated as follows:
  ○: easily released
  Δ: released with difficulty
  x: released with difficulty as much as the substrate or the glass was broken 2. Endurance Reliability The polarizing plate (90 mm×170 mm) coated with the pressure-sensitive adhesive prepared in Example 1 above was attached to both sides of a glass substrate (110 mm×190 mm×0.7 mm) with each optical absorbing axis crossed. The glass substrate was subjected to a clean room work at the applied pressure of about 5 kg/cm$^2$ so that bubbles or impurities might not be generated. In order to evaluate moisture-heat resistance of the specimens, they were left at a temperature of 60° C. and a relative humidity of 90% for 1,000 hours and then observed about formation of bubbles or releases. Also, in order to evaluate heat resistance of the specimens, they were left at 80° C. for 1,000 hours and then observed about formation of bubbles or releases. The specimens were left at room temperature for 24 hours immediately before evaluating their states. Also, the prepared pressure-sensitive adhesive polarizing plates above were left for 5 or more months and then the reliability was evaluated in accordance with the above method. The evaluation standard of endurance reliability was as follows:
  ○: No bubble or release phenomenon was observed.
  Δ: A few bubbles or release phenomenon was occurred.
  x: A large quantity of bubbles or release phenomenon was occurred.

3. Uniformity of Light Transmission (Light Leakage)

To investigate uniformity of light transmission, the glass substrates were observed about whether light was leaked in a dark room using a backlight. The polarizing plate (310 mm×385 mm) coated with the pressure-sensitive adhesive prepared in Example 1 above was attached to both sides of a glass substrate with each optical absorbing axis crossed. These specimens were stored under conditions at a temperature of 60° C. and a relative humidity of 90%, and a temperature of 80° C. for 500 hours, and then uniformity of light transmission was evaluated. Uniformity of light transmission was evaluated with the following standard:
  ⊙: Non-uniformity phenomenon of light transmission was difficultly determined by the naked eye.
  ○: A few non-uniformity phenomenon of light transmission was present.
  Δ: Some non-uniformity phenomenon of light transmission was present.
  x: A large quantity of non-uniformity phenomenon of light transmission was present.

TABLE 2

| | | Example | | | Comparative Example | | | |
|---|---|---|---|---|---|---|---|---|
| | | 1 | 2 | 3 | 1 | 2 | 3 | 4 |
| Formulation (part by weight) | Preparation Example 1 | 20 | | | 5 | | | |
| | Preparation Example 2 | | 30 | 40 | | | | 100 |
| | Preparation Example 3 | | | | | 20 | | |
| | Preparation Example 4 | | | | | | 30 | |
| | Preparation Example 5 | 80 | | | 95 | | | |
| | Preparation Example 6 | | 70 | 60 | | | | |
| | Preparation Example 7 | | | | | 80 | | |
| | Preparation Example 8 | | | | | | 70 | |
| | Cross-linking agent | 0.1 | 0.1 | 0.1 | 0.1 | 0.1 | 0.1 | 0.1 |
| Re-releasability | | ○ | ○ | ○ | X | X | ○ | X |
| Endurance reliability | | ○ | ○ | ○ | X | Δ | ○ | ○ |
| Light leakage | | ⊙ | ⊙ | ⊙ | ⊙ | ⊙ | X | ○ |

As shown in the results of Table 2, Examples 1 to 3 of the present invention represented an excellent endurance reliability and workability (re-releasability), and represented an excellent low light leakage property. On the other hand, in case of Comparative Example 1, the amount of cross-linkable polymer is so low that the low light leakage property is excellent, but the re-releasability and the endurance reliability are poor. In case of Comparative Example 2, the aromatic and acrylic ester monomers are introduced in too large quantity, so that the low light leakage property is excellent, but the re-releasability and the endurance reliability are poor. In addition, in case of Comparative Example 3, the amounts of aromatic and acrylic esters are so low that the low light leakage property is poor. In case of Comparative Example 4, the cross-linkable polymer is used alone, so that the re-releasability is very poor.

INDUSTRIAL APPLICABILITY

The present invention relates to an acrylic pressure-sensitive adhesive composition for a polarizing plate, and has an excellent low light leakage property, without changing major properties such as endurance reliability and re-workability under a high temperature condition and a high temperature and humidity condition. Therefore, if said pressure-sensitive adhesive composition is applied to a polarizing plate of liquid crystal display device, the light leakage phenomenon occurred after using for a long time may be prevented.

The present invention is explained in detail, with reference to the described embodiments above. It is evident to one skilled in the art that various modifications and variations are allowed within the scope and the technical spirit of the present invention. Such modifications and variations should be pertained to the attached claims.

The invention claimed is:

1. An acrylic pressure-sensitive adhesive composition for a polarizing plate comprising:
   an acrylic copolymer (A) containing i) 50 to 75 parts by weight of an alkyl(meth)acrylic acid ester monomer having alkyl of 2 to 14 carbon atoms, ii) 25 to 50 parts by weight of an acrylic ester monomer including an aromatic group copolymerizable with said acrylic monomer, and iii) 0.1 to 10 parts by weight of a vinyl or acrylic monomer including a cross-linkable functional group with respect to 100 parts by weight of the acrylic copolymer (A);
   an acrylic copolymer (B), that does not contain a cross-linkable functional group, consisting of i) 50 to 75 parts by weight of an alkyl(meth)acrylic acid ester monomer having alkyl of 2 to 14 carbon atoms, and ii) 25 to 50 parts by weight of an acrylic ester monomer including an aromatic group copolymerizable with said acrylic monomer with respect to 100 parts by weight of the acrylic copolymer (B); and
   a multi-functional cross-linking agent (C) cross-linkable with an acrylic monomer including a cross-linkable functional group of iii) above;
   wherein a weight ratio of the acrylic copolymer (A) and the acrylic copolymer (B) is 1:9 to 4:1, and weight average molecular weights of acrylic copolymer (A) and acrylic copolymer (B) are each independently 800,000 to 2,000,000.

2. The acrylic pressure-sensitive adhesive composition of claim 1, wherein i) alkyl(meth)acrylic acid ester monomers in acrylic copolymer (A) and acrylic copolymer (B) are each independently one or more selected from the group consisting of ethyl (meth)acrylate, n-propyl (meth)acrylate, isopropyl (meth)acrylate, n-butyl (meth)acrylate, t-butyl (meth)acrylate, seo-butyl (meth)acrylate, pentyl (meth)acrylate, 2-ethylhexyl (meth)acrylate, n-octyl (meth)acrylate, ismtyl (meth)acrylate, isononyl (meth)acrylate, lauryl (meth)acrylate, and tetradecyl (meth)acrylate.

3. The acrylic pressure-sensitive adhesive composition of claim 1, wherein ii) acrylic ester monomers containing an aromatic group in acrylic copolymer (A) and acrylic copolymer (B) are each independently a compound of Formula 1:

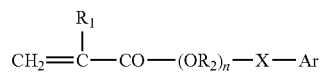

wherein,
$R_1$ represents hydrogen or a methyl group,
$R_2$ represents an alkylene group having 1 to 12 carbon atoms,
n represents an integer of 0 to 3,
X represents an oxygen atom, a sulfur atom, or an alkylene group of 1 to 4 carbon atoms, and
Ar represents an aromatic group unsubstituted or substituted with halogen or alkyl of 1 to 12 carbon atoms.

4. The acrylic pressure-sensitive adhesive composition of claim 3, wherein said compound of Formula 1 is one or more selected from the group consisting of phenoxy ethyl (meth)acrylate, benzyl (meth)acrylate, 2-phenylthio-1-ethyl (meth)acrylate, 6-(4,6-dibromo-2-isopropylphenoxy)-1-hexyl (meth)acrylate, 6-(4,6-dibromo-2-seo-butylphenoxy)-1-hexyl (meth)acrylate, 2,6-dibromo-4-nonylphenyl (meth)acrylate, 2,6-dibromo-4-dodecyl phenyl (meth)acrylate, 2-(1-haphtyloxy)-1-ethyl (meth)acrylate, 2-(2-naphtyloxy)-1-ethyl (meth)acrylate, 6-(1-naphtyloxy)-1-hexyl (meth)acrylate, 6-(2-naphtyloxy)-1-hexyl (meth)acrylate, 8-(1-naphtyloxy)-1-octyl (meth)acrylate, and 8-(2-naphtyloxy)-1-octyl (meth)acrylate.

5. The acrylic pressure-sensitive adhesive composition of claim 1, wherein iii) a vinyl or acrylic monomer maintaining a cross-linkable functional group in acrylic copolymer (A) maintains an acid group or a hydroxyl group within its structure.

6. The acrylic pressure-sensitive adhesive composition of claim 5, wherein the vinyl or acrylic monomer maintaining an acid group is one or more selected from the group consisting of (meth)acrylic acid, acrylic acid dimmer, carboxyethyl acrylate, carboxpentyl acrylate, itaconic acid, maleic acid, fumaric acid, crotonic acid, maleic anhydride, itaconic anhydride, styrene sulfonic acid, allyl sulfonic acid, 2-(meth)acrylamide-2-methyl propane sulfonic acid, (meth-d)acrylamide propane sulfonic acid, sulfopropyl (meth)acrylate, (meth)acryloyloxy naphthale sulfonic acid, and 2-hydroxyethyl acryloyl phosphate.

7. The acrylic pressure-sensitive adhesive composition of claim 5, wherein the vinyl or acrylic monomer maintaining a hydroxyl group is one or more selected from the group consisting of 2-hydroxyethyl (meth)acrylate, 2-hydroxypropyl (meth)acrylate, 4-hydroxbutyl (meth)acrylate, 2-hydroxyethylene glycol (meth)acrylate, and 2-hydroxypropylene glycol (meth)acrylate.

8. The acrylic pressure-sensitive adhesive composition of claim 1, wherein the multi-functional cross-linking agent (C) is included in an amount of 0.01 to 10 parts by weight based on the acrylic copolymer (A).

9. The acrylic pressure-sensitive adhesive composition of claim 8, wherein the multi-functional cross-linking agent (C) is one or more selected from the group consisting of isocyanate compounds, epoxy compounds, aziridine compounds, and metal chelating compounds.

10. The acrylic pressure-sensitive adhesive composition of claim 9, wherein the multi-functional cross-linking agent (C) is one or more isocyanate compounds selected from the group consisting of to lylene diisocyanate, xylene diisocyanate, diphenylmethane diisocyanate, hexamethylene diisocyanate, isoform diisocyanate, tetramethylxylene diisocyanate, naphthalene diisocyanate, and their reactants with polyol.

11. The acrylic pressure-sensitive adhesive composition of claim 1, further comprising 0.005 to 5 parts by weight of silane coupling agent based on 100 parts by weight of total acrylic copolymers.

12. The acrylic pressure-sensitive adhesive composition of claim 11, wherein the silane coupling agent is one or more selected from the group consisting of g-glycydoxypropyl trimethoxysilane, g-glycydoxypropyl methyldiethoxysilane, g-glycydoxypropyl tri-ethoxysilane, 3-mercaptopropyl trimethoxysilane, vinyl trimethoxysilane, vinyl tri-ethoxysilane, g-methacryloxypropyl trimethoxsilane, g-methacryloxpropyl tri-ethoxsilane, g-aminopropyl triethoxysilane, 3-isocyanatepropyl triethoxysilane, and g-acetoacetatepropyl trimethoxysilane.

13. The acrylic pressure-sensitive adhesive composition of claim 1, further comprising 1 to 100 parts by weight of tackifier resin based on 100 parts by weight of total acrylic copolymers.

14. The acrylic pressure-sensitive adhesive composition of claim 13, wherein the tackifier resin is one or more selected from the group consisting of a (hydrogenated) hydrocarbon resin, a (hydrogenated) rosin resin, a (hydrogenated) rosin ester resin, a (hydrogenated) terpene resin, a (hydrogenated) terpene phenol resin, a polymerized rosin resin, and a polymerized rosin ester resin.

15. A polarizing plate comprising
a polarizing film; and
a pressure-sensitive adhesive layer maintaining an acrylic pressure-sensitive adhesive composition according to claim 1.

16. The polarizing plate of claim 15, further comprising one or more layers selected from the group consisting of a protective layer, a reflective layer, a phase retardation plate, a compensation film for wide view angle and a brightness enhancing film.

17. A liquid crystal display device comprising liquid crystal panel in which a polarizing plate according to claim 15 is adhered onto one side or both sides of liquid crystal cell.

* * * * *